(12) United States Patent
Ruezinsky et al.

(10) Patent No.: US 7,521,594 B2
(45) Date of Patent: Apr. 21, 2009

US007521594B2

(54) CPC214 GENE PROMOTER SEQUENCES AND METHODS OF USE

(75) Inventors: Diane M. Ruezinsky, Woodland, CA (US); Obed Patty, Marysville, CA (US); Crystal L. Hewitt, Sacramento, CA (US); Wei Wu, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/750,996

(22) Filed: May 18, 2007

(65) Prior Publication Data

US 2008/0028490 A1 Jan. 31, 2008

Related U.S. Application Data

(62) Division of application No. 11/016,360, filed on Dec. 17, 2004, now Pat. No. 7,230,162.

(60) Provisional application No. 60/531,483, filed on Dec. 19, 2003.

(51) Int. Cl.
*C12N 15/82* (2006.01)
*C07H 21/04* (2006.01)
*A01H 5/00* (2006.01)

(52) U.S. Cl. .................. 800/287; 536/24.1; 800/281; 800/298; 800/300.1; 800/278; 435/419; 435/468; 435/320.1

(58) Field of Classification Search ..................... None
See application file for complete search history.

(56) References Cited

U.S. PATENT DOCUMENTS

| 5,164,316 | A | | 11/1992 | McPherson et al. | ....... 435/240.4 |
|---|---|---|---|---|---|
| 5,196,525 | A | | 3/1993 | McPherson et al. | ......... 536/24.1 |
| 5,304,712 | A | * | 4/1994 | Harper, II | ................ 800/320.1 |
| 5,322,938 | A | | 6/1994 | McPherson et al. | ......... 536/24.1 |
| 5,352,605 | A | | 10/1994 | Fraley et al. | ............. 435/240.4 |
| 5,359,142 | A | | 10/1994 | McPherson et al. | ......... 800/205 |
| 5,378,619 | A | | 1/1995 | Rogers | .................... 435/172.3 |
| 5,391,725 | A | | 2/1995 | Coruzzi et al. | ............. 536/24.1 |
| 5,424,200 | A | | 6/1995 | McPherson et al. | ......... 435/70.1 |
| 5,428,147 | A | | 6/1995 | Barker et al. | ................ 536/24.1 |
| 5,447,858 | A | | 9/1995 | Key et al. | ................. 435/172.3 |
| 5,589,583 | A | | 12/1996 | Klee et al. | .................. 536/24.1 |
| 5,608,144 | A | | 3/1997 | Baden et al. | ................. 800/205 |
| 5,614,399 | A | | 3/1997 | Quail et al. | .............. 435/172.3 |
| 5,633,435 | A | | 5/1997 | Barry et al. | .................. 800/205 |
| 5,633,441 | A | | 5/1997 | De Greef et al. | ............ 800/205 |
| 5,898,096 | A | | 4/1999 | Klee et al. | .................. 800/205 |
| 6,096,950 | A | | 8/2000 | John | ......................... 800/314 |
| 6,232,526 | B1 | | 5/2001 | McElroy et al. | ............. 800/278 |
| 6,342,657 | B1 | * | 1/2002 | Thomas et al. | .............. 800/287 |

OTHER PUBLICATIONS

Donald et al. Mutation of either G box or I box sequences profoundly affects expression from the Arabidopsis rbcS-1A promoter. (1990) EMBO J. vol. 9; pp. 1717-1726.*
Benfey et al. The cauliflower mosaic virus 35S promoter: combinatorial regulation of transcription in plants. (1990) Science vol. 250; pp. 959-966.*
Kim et al. A 20 nucleotide upstream element is essential for the nopaline synthase (nos) promoter activity. (1994) Plant Mol. Biol. vol. 24; pp. 105-117.*
Whitelaw et al. OGADF63TCB ZM2_0.7_1.5_KB Zea mays genomic clone ZMMBMa0034L06, genomic survey sequence. (2002) GenBank Accession BZ543287, pp. 1-2.*
Maiti et al. Promoter/leader deletion analysis and plant expression vectors with the figwort mosaic virus (FMV) full length transcript (FLt) promoter containing single or double enhancer domains. (1997) Transgen. Res. vol. 6; pp. 143-156.*
Stalberg et al. Deletion analysis of a 2S seed storage protein promoter of *Brassica napus* in transgenic tobacco. (1993) PMB; vol. 23, pp. 671-683.*
Boutilier et al. Ectopic expression of BABY BOOM triggers a conversion from vegetative to embryonic growth. (2002) The Plant Cell; vol. 14, pp. 1737-1749.*
Kim et al., "A 20 nucleotide upstream element is essential for the nopaline synthase (nos) promoter activity," *Plant Molecular Biology*, 24:105-117, 1994.
Whiteclaw et al., GenBank Accession CG098141, 2003.
Whiteclaw et al., GenBank Accession BZ718159, 2003.

* cited by examiner

*Primary Examiner*—Cathy Kingdon Worley
(74) *Attorney, Agent, or Firm*—Sonnenschein Nath & Rosenthal LLP

(57) ABSTRACT

The present invention relates to polynucleotide molecules for regulating gene expression in plants. In particular, the invention relates to CPC214 promoters isolated from *Zea mays* that are useful for regulating gene expression of heterologous polynucleotide molecules in plants. The invention also relates to expression constructs and transgenic plants containing the heterologous polynucleotide molecules.

35 Claims, 3 Drawing Sheets

SEQUENCE LISTING

```
<160> NUMBER OF SEQ ID NOS: 23

<210> SEQ ID NO 1
<211> LENGTH: 481
<212> TYPE: DNA
<213> ORGANISM: Zea mays
<220> FEATURE:
<221> NAME/KEY: modified_base
<222> LOCATION: (9)
<223> OTHER INFORMATION: n = a, c, g or t/u

<400> SEQUENCE: 1
cctcgaggnc ggccgggggc aacgttctct aacaagaagc acagatagca acacaataac      60
aacaatggtc gcgttcgagc gtagtaggag cacaaccaca gtggtgctcc tcgtcctttt     120
```

-continued

```
gatgccgcta ctgctgtcat catccaccgc gtcggaggca cacatccaga agaaatggag    180 accccaata atctatccat ggatgccccc gataatctat ccatcgccga taccacctcc     240
```
(note: second line begins "acccccaata")

```
gatgccgcta ctgctgtcat catccaccgc gtcggaggca cacatccaga agaaatggag    180
acccccaata atctatccat ggatgccccc gataatctat ccatcgccga taccacctcc    240
acaccatggg cgcgacttgg acttgcccct catgaacaac aagcacaccc caccggcgtc    300
acagcaagat gaccaagctg ttgtcggctc gttgcagcct tagctttgaa tgtgttgcat    360
gggttgttat atttatggtg aggaataaat ttaattaact ttgaataatt ccaatgtat     420 ttgagtgagc cgagctaaac gcatgagact tgcggacaaa aaaaaaaaa aaaaagcggc     480 c                                                                    481
```

<210> SEQ ID NO 2
<211> LENGTH: 25
<212> TYPE: DNA
<213> ORGANISM: Artificial Sequence
<220> FEATURE:
<223> OTHER INFORMATION: Primer
<400> SEQUENCE: 2

```
attcaaagct aaggctgcaa cgagc                                           25
```

<210> SEQ ID NO 3
<211> LENGTH: 341
<212> TYPE: DNA
<213> ORGANISM: Zea mays
<400> SEQUENCE: 3

```
ggcaacgttc tctgacaaga agcacagata gcaacaacaa taacaacaat ggtcgcgttc    60
gagcgtagca ggagcacaac caccgtggtg ctcctcgtcc ttttgatgcc gctactgctg   120
tcaacatcca ccgcgtcgga ggcacacatc cagaagaaat ggagaccccc aataatctat   180
ccatggatgc ccccgataat ctatccatcg ccgataccac ctccacacca tgggcgcgac   240
ttggacttgc cctccatgaa caacaagcac accccaccag cgtcacagca agacgaccaa   300
gctgctgtca gctcgttgca gccttagctt tgaataaggg c                        341
```

<210> SEQ ID NO 4
<211> LENGTH: 25
<212> TYPE: DNA
<213> ORGANISM: Artificial Sequence
<220> FEATURE:
<223> OTHER INFORMATION: Primer
<400> SEQUENCE: 4

```
gcaacacatt caaagctaag gctgc                                           25
```

<210> SEQ ID NO 5
<211> LENGTH: 26
<212> TYPE: DNA
<213> ORGANISM: Artificial Sequence
<220> FEATURE:
<223> OTHER INFORMATION: Primer
<400> SEQUENCE: 5

```
ggaggtggta tcggcgatgg atagat                                          26
```

<210> SEQ ID NO 6
<211> LENGTH: 27
<212> TYPE: DNA
<213> ORGANISM: Artificial Sequence
<220> FEATURE:
<223> OTHER INFORMATION: Primer
<400> SEQUENCE: 6

```
taacaaccca tgcaacacat tcaaagc                                      27

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
ggtggtatcg gcgatggata gatta                                        25

<210> SEQ ID NO 8
<211> LENGTH: 1265
<212> TYPE: DNA
<213> ORGANISM: Zea mays

<400> SEQUENCE: 8
acgatgctgt cctcgacgac agcggcagtg cgctggttgg gtggaagcat cgtccaacaa    60
ccccaaccct ttcgtgaccc tcctccgcgg cattggggtc catggttagt tatcctctgc   120
cacataacat ggggcaagcg tcgtggtctc ctctgccgcc ctggattccc ctaccaccac   180
catgcgccac cgtcggagac atactgtcca tcggcaccga gtaattattg attgattcat   240
tggaatgtta ggacaagatg gccgatttag gggaaaaata tgcgacgcca ttgatggacc   300
ggcgtgctac tgaattgttt tacacatcta aatctggccc aataagccca tatgattggt   360
tgatgaggca gaatatattt ttagttcatt atgcttatga tgaaataaat taatcatctc   420
aaacagatat gattgttgta tatatctcat tgctgtcaag aaatgaaata attcaaatct   480
acatggtagt tatcttagtt gtgtttgcct actaattaaa tgaaggtagg catctttgga   540
tgccaaatga ctcgtcaagc taaatgagac ggacatgact tcctctgttg atactattaa   600
tgaaggtgga cgtctttgat gccaaatgac ttatcaagct aaattttagc tactcaaaag   660
taaaataact ctatgctagt ggttgaccta agtatttac ctatgtaaat ttgtttacaa    720
aggcgacatc gttatgccaa taatgacccg ccgcaatcat acgccaatgg aacacatcat   780
ttccataatc tttcatgtca gcatttcaca aaaccaccta tgaagataca aaaactacca   840
ctagtaaaac ctatttctat actagtggtg gtcgaaactt gagaaagttt gatggccaag   900
aatcataaag cgacttgtaa ttacaattag ctaacataga taataaatta ttatagaaac   960
agacggtagt tcaaggcttg aagttggatc acaaagatag aaattttttta atgaggttaa  1020 attgacaaac acgaaagaga gcaaagtata ggagcacatt aaattcattc caatgttgat  1080
tgtccatcta tatttatgca acataatatt tgcacctctc ttagagcaaa aattaaatta  1140
ccacctagtt tagatgacaa ccatctatcc atgctaaatt taagcactag agagtcgaca  1200
ctatatatac acacatatat gtggtataac accggcaacg ttctctgaca agaagcacag  1260
atagc                                                             1265

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
ctcgagcggc ccaataagcc catatgattg g                                  31
```

<210> SEQ ID NO 10
<211> LENGTH: 43
<212> TYPE: DNA
<213> ORGANISM: Artificial Sequence
<220> FEATURE:
<223> OTHER INFORMATION: Primer

<400> SEQUENCE: 10
ccatggagat ctgctatctg tgcttcttgt cagagaacgt tgc                43

<210> SEQ ID NO 11
<211> LENGTH: 949
<212> TYPE: DNA
<213> ORGANISM: Zea mays

<400> SEQUENCE: 11
ctcgagcggc ccaataagcc catatgattg gttgatgagg cagaatatat ttttagttca    60
ttatgcttat gatgaaataa attaatcatc tcaaacagat atgattgttg tatatatctc   120
attgctgtca agaaatgaaa taattcaaat ctacatggta gttatcttag ttgtgtttgc   180
ctactaatta aatgaaggta ggcatctttg gatgccaaat gactcgtcaa gctaaatgag   240
acggacatga cttcctctgt tgatactatt aatgaaggtg gacgtctttg atgccaaatg   300
acttatcaag ctaaattta gctactcaaa agtaaaataa ctctatgcta gtggttgacc   360
taagtatttt acctatgtaa atttgtttac aaaggcgaca tcgttatgcc aataatgacc   420
cgccgcaatc atacgccaat ggaacacatc atttccataa tctttcatgt cagcatttca   480
caaaaccacc tatgaagata caaaaactac cactagtaaa acctatttct atactagtgg   540
tggtcgaaac ttgagaaagt ttgatggcca agaatcataa agcgacttgt aattacaatt   600
agctaacata gataataaat tattatagaa acagacggta gttcaaggct tgaagttgga   660
tcacaaagat agaaattttt taatgaggtt aaattgacaa acacgaaaga gagcaaagta   720
taggagcaca ttaaattcat tccaatgttg attgtccatc tatatttatg caacataata   780
tttgcacctc tcttagagca aaaattaaat taccacctag tttagatgac aaccatctat   840
ccatgctaaa tttaagcact agagagtcga cactatatat acacacatat atgtggtata   900
acaccggcaa cgttctctga caagaagcac agatagcaga tctccatgg              949

<210> SEQ ID NO 12
<211> LENGTH: 110
<212> TYPE: DNA
<213> ORGANISM: Zea mays

<400> SEQUENCE: 12
taacacctga tgaatccttt attatacatt gcttttatt ttcaccttgc tacagcatga    60
caaagaccaa aaaaacgag caggctatat tcagatccat ttcatgaatt               110

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
cgagcaggct atattcagat ccatttcatg                                    30

<210> SEQ ID NO 14
<211> LENGTH: 400

```
<212> TYPE: DNA
<213> ORGANISM: Zea mays

<400> SEQUENCE: 14
acagatacag gctcaaaacc aagcaacgcc gcgccgacgc aagactacca gagatgaaga      60
ccggcctcgt gacactacag ctactcacca tcaccatgtt tctcgtgcta tcgtcgcatg     120
cagatagcac ggtggccagg actgggccag actacttcca ggacacctgc tcggcgagga    180
tttcttcggg ggcacggtgc cagcctagca agtgcgccgc ggactgcacc aggcaattca    240
ggggcggcgt gggcagctgt gaccgctcgg ggtgtatgtg cgtctacacc tgccctgcgg    300
tctcgccact ggcaaagaac gaatcaatcg cgtgaccctg actgtctcga tgcataagta    360
gtgacggacg ggctagtagc cgacctgtga cggctttgcg                          400

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
cgagaaacat ggtgatggtg agtagctg                                        28

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
ggtcttcatc tctggtagtc ttgcgtcg                                        28

<210> SEQ ID NO 17
<211> LENGTH: 1316
<212> TYPE: DNA
<213> ORGANISM: Zea mays

<400> SEQUENCE: 17
tagaatgcac caaatccatg aagaaaacaa tgtcaaaccc tacttggcgt gcgaaatagc      60
accatggtac gacatgtggg tacgaaaggt acccaaaaca tgaaaagtgt aacagataga    120
ccaaatgcat aaactagata tgcgttgaat ttgggtgcac aacatgagga caatttagag    180
atgtccaggt cgtagtgtgc gtagtacctt atgttctctt gtgtgtaata gatttataaa    240
catataagtg aagaagatta aaatctcaaa tatcatctga gcatcatgat cacccagctc    300
tatcttctcc tatatgcctg cccttagaag attggaaatc ctgaagtcta taatcgattc    360
tcttctatga tgatgaacct ccattttatgt tgctatactc cccattttta tagaccaagg    420
gaggataaat gattaaatat cgattggact atgggtttct gttagctgtg gcccaacaac    480
tccaatttta tcctagtcgt ggagccattc atagcgcccc atccccaggg cccttagcc     540 taaggtttta cattattctt atgaatgaca gtggtcgaaa gaacctaagt gtggaagcat    600
ctcgaagcct agagtgccct ggggctctgg tggtctagta ttttaggttg tttgtttggg    660
atataatggt tgaacaatta tttttcagat ggccttgaga tcaagctctt caaagtgata    720
ggaccttgca tttgtcggag tcaaaatatc ctagggcatg gggtcgtggg agcgcatgtc    780
ctgcagtagc aagaccctc cccctctcct acgatttatt tctttgggat catcgaagac     840
```

| | |
|---|---:|
| gtcatgacaa cacccgatga ggccttgttc gattattcct attgtatatg gattggatgt | 900 |
| gattggaaaa aattagaaga actttgactt acttgggatt taaacccacc caatctcact | 960 |
| caatccacat ggattgggag ctaaccgaac aagccctgat atggtatggt ttttccatgg | 1020 |
| caccggcaat acaacgtaca caattagcat ataattgcag ttaacaaaac aataaataaa | 1080 |
| caacattttt aaaattccta aaagtagcta gcaatcaata gcgatttcaa agctcacac | 1140 |
| cataaacacg tgataccaaa gagcaatttc cctatataac cccttcccgt cggacccgtc | 1200 |
| aaatacatac agatacaggc tcaaaaccaa gcaacgccgc ccgacgcaa gactaccaga | 1260 |
| gatgaagacc ggcctcgtga cactacagct actcaccatc accatgtttc tcgtgc | 1316 |

<210> SEQ ID NO 18
<211> LENGTH: 1196
<212> TYPE: DNA
<213> ORGANISM: Zea mays

<400> SEQUENCE: 18

| | |
|---|---:|
| ggtacgacat gtgggtacga aggtaccca aacatgaaa agtgtaacag atagaccaaa | 60 |
| tgcataaact agatatgcgt tgaatttggg tgcacaacat gaggacaatt tagagatgtc | 120 |
| caggtcgtag tgtgcgtagt accttatgtt ctcttgtgtg taatagattt ataaacatat | 180 |
| aagtgaagaa gattaaaatc tcaaatatca tctgagcatc atgatcaccc agctctatct | 240 |
| tctcctatat gcctgccctt agaagattgg aaatcctgaa gtctataatc gattctcttc | 300 |
| tatgatgatg aacctccatt tatgttgcta tactccccca ttttatagac caagggagga | 360 |
| taaatgatta aatatcgatt ggactatggg tttctgttag ctgtggccca acaactccaa | 420 |
| ttttatccta gtcgtggagc cattcatagc gccctatccc cagggcccct tagcctaagg | 480 |
| ttttacatta ttcttatgaa tgacagtggt cgaaagaacc taagtgtgga agcatctcga | 540 |
| agcctagagt gccctgggc tctggtggtc tagtatttta ggttgtttgt ttgggatata | 600 |
| atggttgaac aattattttt cagatggcct tgagatcaag ctcttcaaag tgataggacc | 660 |
| ttgcatttgt cggagtcaaa atatcctagg gcatggggtc gtgggagcgc atgtcctgca | 720 |
| gtagcaagac ccctccccct ctcctacgat ttatttcttt gggatcatcg aagacgtcat | 780 |
| gacaacaccc gatgaggcct tgttcgatta ttcctattgt atatggattg gatgtgattg | 840 |
| gaaaaaatta gaagaacttt gacttacttg ggatttaaac ccacccaatc tcactcaatc | 900 |
| cacatggatt gggagctaac cgaacaagcc ctgatatggt atggtttttc catggcaccg | 960 |
| gcaatacaac gtacacaatt agcatataat tgcagttaac aaaacaataa ataacaaca | 1020 |
| ttttaaaat tcctaaaagt agctagcaat caatagcgat ttcaaaagct cacaccataa | 1080 |
| acacgtgata ccaaagagca atttccctat ataaccccctt cccgtcggac ccgtcaaata | 1140 |
| catacagata caggctcaaa accaagcaac gccgcgccga cgcaagacta ccagag | 1196 |

<210> SEQ ID NO 19
<211> LENGTH: 399
<212> TYPE: DNA
<213> ORGANISM: Zea mays

<400> SEQUENCE: 19

| | |
|---|---:|
| ccttgttcga ttattcctat tgtatatgga ttggatgtga ttggaaaaaa ttagaagaac | 60 |
| tttgacttac ttgggatta aacccaccca atctcactca atccacatgg attgggagct | 120 |
| aaccgaacaa gccctgatat ggtatggttt tccatggca ccggcaatac aacgtacaca | 180 |
| attagcatat aattgcagtt aacaaaacaa taaataaaca cattttaa aattcctaaa | 240 |

```
agtagctagc aatcaatagc gatttcaaaa gctcacacca taaacacgtg ataccaaaga    300
gcaatttccc tatataaccc cttcccgtcg gacccgtcaa atacatacag atacaggctc    360
aaaaccaagc aacgccgcgc cgacgcaaga ctaccagag                           399
```

```
<210> SEQ ID NO 20
<211> LENGTH: 962
<212> TYPE: DNA
<213> ORGANISM: Zea mays

<400> SEQUENCE: 20
ggtacgacat gtgggtacga aaggtaccca aaacatgaaa agtgtaacag atagaccaaa     60
tgcataaact agatatgcgt tgaatttggg tgcacaacat gaggacaatt tagagatgtc    120
caggtcgtag tgtgcgtagt acctcatgtt ctcttgtgtg taatagattt ataaacatat    180
aagtgaagaa gattaaaatc tcaaatatca tctgagcatc atgatcaccc agctctatct    240
tctcctatat gcctgcccct agaagattgg aaatcctgaa gtctataatc gattctcttc    300
tatgatgatg aacctccatt tatgttgcta tactccccca ttttatagac caagggagga    360
taaatgatta aatatcgatt ggactatggg tttctgttag ctgtggccca acaactccaa    420
ttttatccta gtcgtggagc cattcatagc gccctatccc cagggcccct tagcctaagg    480
ttttacatta ttcttatgaa tgacagtggt cgaaagaacc taagtgtgga agcatctcga    540
agcctagagt gccctgggc tctggtggtc tagtatttta ggttgtttgt ttgggatata    600
atggttgaac aattatttt cagatggcct tgagatcaag ctcttcaaag tgataggacc    660
ttgcatttgt cggagtcaaa atatcctagg gcatggggtc gtgggagcgc atgtcccatg    720
gcaccggcaa tacaacgtac acaattagca tataattgca gttaacaaaa caataaataa    780
acaacatttt taaaattcct aaaagtagct agcaatcaat agcgatttca aaagctcaca    840
ccataaacac gtgataccaa agagcaattt ccctatataa ccccttcccg tcggacccgt    900
caaatacata cagatacagg ctcaaaacca agcaacgccg cgccgacgca agactaccag    960
ag                                                                   962
```

```
<210> SEQ ID NO 21
<211> LENGTH: 801
<212> TYPE: DNA
<213> ORGANISM: Oryza sativa

<400> SEQUENCE: 21
tgactgaagt gtagcaattc ctttattatt atccatttgg tgaattagtc catggccaat     60
gctccatcgt gtcacgtacc ccggcactcc ttgtaggaat caggccaaac aagcaacgcc    120
ttgtgtcctt atgcaaggag acatgactct tctacaagaa aggacgcaac accccggagc    180
atggcgcagc tgcgagatga gggtgcgggt tggggcagcg tgtctaggag ctcatggctt    240
gagcttggtg ttgcggtccc ctcgttccaa tcagtacgta gtacaagatt gacctctcgc    300
cctaatctca cttcgttatt tggtaaggct agaaattacc tctctatgac tgttgggttc    360
tggctacttg cattatgggc tataacatct ttaacatatg ctttggattg actatgaccc    420
atctaaacat tttccatgcc atacggagca tatgcgcttt ttttttctcg tgaaaattga    480
caaattaaaa tgcaccgaaa tatcaccttt aattggtact attgattagg taccaatttg    540
gtacaaccct taatacaagg ccactatata atcctaaaga tcagcacaaa cgaatatagc    600
agtatcaatg ccaattactc ctgaaattaa acccgttccc gttatccata tccatacaac    660
```

-continued

```
ttactgtagt aagtgattcc aaaaataata cgaacaacaa cactataaac gccacactcc    720
cattcggtac acctaaaaga aacaaagctg cagctaagca ccggtagcag tagcagaagt    780
cacaaggaaa aaaaaaagcc a                                              801
```

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
ctcgagggta cgacatgtgg gtacgaaagg                                    30

<210> SEQ ID NO 23
<211> LENGTH: 27
<212> TYPE: DNA
<213> ORGANISM: Artificial Sequence
<220> FEATURE:
<223> OTHER INFORMATION: Primer

<400> SEQUENCE: 23
tctagactct ggtagtcttg cgtcggc                                       27

US 7,521,594 B2

CPC214 GENE PROMOTER SEQUENCES AND METHODS OF USE

PRIORITY INFORMATION

This application is a divisional application of application Ser. No. 11/016,360, filed Dec. 17, 2004 now U.S. Pat. No. 7,230,162, which claims the priority of U.S. Provisional Application Ser. No. 60/531,483, filed Dec. 19, 2003, the entire disclosures of which are each specifically incorporated herein by reference.

FIELD OF THE INVENTION

The invention relates to the field of plant molecular biology and plant genetic engineering and more specifically relates to polynucleotide molecules useful for the expression of transgenes in plants.

BACKGROUND OF THE INVENTION

One of the goals of plant genetic engineering is to produce plants with agronomically desirable characteristics or traits. Advances in genetic engineering have provided the requisite tools to transform plants to contain and express foreign genes. The technological advances in plant transformation and regeneration have enabled researchers to take an exogenous polynucleotide molecule, such as a gene from a heterologous or native source, and incorporate that polynucleotide molecule into a plant genome. The gene can then be expressed in a plant cell to exhibit the added characteristic or trait. In one approach, expression of a gene in a plant cell or a plant tissue that does not normally express such a gene may confer a desirable phenotypic effect. In another approach, transcription of a gene or part of a gene in an antisense orientation may produce a desirable effect by preventing or inhibiting expression of an endogenous gene.

Promoters are polynucleotide molecules that comprise the 5' regulatory elements that play an integral part in the overall expression of genes in living cells. Isolated promoters that function in plants are useful for modifying plant phenotypes through the methods of genetic engineering. The first step in the process to produce a transgenic plant includes the assembly of various genetic elements into a polynucleotide construct. The construct includes a transcribable polynucleotide molecule (gene of interest) that confers a desirable phenotype when expressed (transcribed) in the plant cells by a promoter that is operably linked to the gene of interest. A promoter in a construct may be homologous or heterologous to the gene of interest also contained therein. The construct is then introduced into a plant cell by various methods of plant transformation to produce a transformed plant cell that may be regenerated into a transgenic plant. The promoter controls expression of the gene of interest to which the promoter is operably linked and thus affects the characteristic or trait conferred by the expression of the transgene in plants.

For production of transgenic plants with various desired characteristics, it would be advantageous to have a variety of promoters to provide gene expression such that a gene is transcribed efficiently in the amount necessary to produce the desired effect. The commercial development of genetically improved germplasm has also advanced to the stage of introducing multiple traits into crop plants, often referred to as a gene stacking approach. In this approach, multiple genes conferring different characteristics of interest can be introduced into a plant. It is often desired when introducing multiple genes into a plant that each gene is modulated or controlled for optimal expression, leading to a requirement for diverse regulatory elements. In light of these and other considerations, it is apparent that optimal control of gene expression and regulatory element diversity are important in plant biotechnology.

A variety of different types or classes of promoters can be used for plant genetic engineering. Promoters can be classified on the basis of characteristics such as temporal or developmental range, levels of transgene expression, or tissue specificity. For example, promoters referred to as constitutive promoters are capable of transcribing operably linked genes efficiently and expressing those genes in multiple tissues. Different types of promoters can be obtained by isolating the upstream 5' regulatory regions of genes that are transcribed and expressed in the desired manner, e.g., constitutive, tissue enhanced, or developmentally induced.

Numerous promoters active in plant cells have been described in the literature. These include the nopaline synthase (nos) promoter and octopine synthase (ocs) promoters carried on tumor-inducing plasmids of *Agrobacterium tumefaciens* and the caulimovirus promoters such as the Cauliflower Mosaic Virus (CaMV) 19S or 35S promoter (U.S. Pat. No. 5,352,605), CaMV 35S promoter with a duplicated enhancer (U.S. Pat. Nos. 5,164,316; 5,196,525; 5,322,938; 5,359,142; and 5,424,200), and the Figwort Mosaic Virus (FMV) 35S promoter (U.S. Pat. No. 5,378,619). These promoters and numerous others have been used in the creation of constructs for transgene expression in plants. Other useful promoters are described, for example, in U.S. Pat. Nos. 5,391,725; 5,428,147; 5,447,858; 5,608,144; 5,614,399; 5,633,441; 6,232,526; and 5,633,435, all of which are incorporated herein by reference.

While previous work has provided a number of promoters useful to direct transcription in transgenic plants, there is still a need for novel promoters with beneficial expression characteristics. In particular, there is a need for promoters that are capable of directing expression of exogenous genes in monocotyledonous seeds during embryogenesis. Many previously identified promoters fail to provide the patterns or levels of expression required to fully realize the benefits of expression of selected genes in transgenic plants. There is, therefore, a need in the art of plant genetic engineering for novel promoters for use in monocots.

SUMMARY OF THE INVENTION

The invention provides, in certain embodiments, the P-Zm-.CEP1, P-Zm.CPC214, P-Zm.214tr1 and P-Zm.CPC214tr2 promoters isolated from *Zea mays* and useful for expression of transgenes of agronomic importance in crop plants. Such promoters may be of particular benefit for directing transgene expression in the embryo, aleurone, or both during kernel development. During kernel development plant embryogenesis is divided into three phases: a proliferation phase in which rapid cell division takes place, followed by the growth phase when cells exit the cell cycle, grow and accumulate storage products, and a final maturation phase in which the embryo undergoes dessication and prepares for dormancy. In maize, the proliferation phase persists through approximately 15 days after pollination ("dap") (stage 1), the growth phase occurs from approximately 16-45 dap (late stage 1 through stage 5) and the maturation phase occurs from approximately 41-55 dap (Randolph, L. F., *J. of Agricultural Research*, 53 (12):881-917 (1936)). Promoters that express in the embryo, aleurone, or both during kernel development are particularly useful for production of transgenic plants with desired seed traits. These include, but are not limited to, altering oil content, protein quality, cell proliferation, or micronutrient quality.

In one embodiment, the present invention provides a promoter comprising a polynucleotide sequence substantially homologous to a polynucleotide sequence selected from the group consisting of SEQ ID NOs: 11, 18, 19, and 20 or any fragments thereof that are capable of regulating transcription of operably linked polynucleotide molecules.

In another embodiment, the invention provides a plant expression construct comprising a promoter comprising a polynucleotide sequence substantially homologous to a polynucleotide sequence selected from the group consisting of SEQ ID NOs: 11, 18, 19, and 20 or any fragments thereof, wherein said promoter is operably linked to a transcribable polynucleotide molecule operably linked to a 3' transcription termination polynucleotide molecule.

In yet another embodiment, the invention provides a transgenic plant stably transformed with a plant expression construct comprising a promoter comprising a polynucleotide sequence substantially homologous to a polynucleotide sequence selected from the group consisting of SEQ ID NOs: 11, 18, 19, and 20 or any fragments thereof, wherein said promoter is operably linked to a transcribable polynucleotide molecule operably linked to a 3' transcription termination polynucleotide molecule.

In another embodiment, the invention provides a method of making a vegetable oil, comprising the steps of incorporating into the genome of an oilseed plant a promoter of the present invention operably linked to a transcribable polynucleotide molecule conferring altered oil and/or protein content, growing the oilseed plant to produce oilseeds, and extracting the oil and/or protein from the oilseed.

The foregoing and other aspects of the invention will become more apparent from the following detailed description and accompanying drawings.

BRIEF DESCRIPTION OF THE SEQUENCES

SEQ ID NO: 1 sets forth a nucleic acid sequence of a *Zea mays* CEP1 EST.

SEQ ID NO: 2 sets forth a primer sequence.

SEQ ID NO: 3 sets forth a nucleic acid sequence of a *Zea mays* CEP1 RACE clone.

SEQ ID NOs: 4-7 set forth primer sequences.

SEQ ID NO: 8 sets forth a nucleic acid sequence of a *Zea mays* cyclin CEP1 genomic sequence.

SEQ ID NOs: 9-10 set forth primer sequences.

SEQ ID NO: 11 sets forth a nucleic acid sequence encoding a *Zea mays* P-Zm.CEP1 promoter.

SEQ ID NO: 12 sets forth a nucleic acid sequence of a *Zea mays* CPC214 AFLP.

SEQ ID NO: 13 sets forth a primer sequence.

SEQ ID NO: 14 sets forth a nucleic acid sequence of a *Zea mays* CPC214 RACE clone.

SEQ ID NOs: 15-16 set forth primer sequences.

SEQ ID NO: 17 sets forth a nucleic acid sequence of a *Zea mays* CPC214 genomic sequence.

SEQ ID NO: 18 sets forth a nucleic acid sequence encoding a *Zea mays* P-Zm.CPC214 promoter.

SEQ ID NO: 19 sets forth a nucleic acid sequence encoding a *Zea mays* P-Zm.CPC214tr1 promoter.

SEQ ID NO: 20 sets forth a nucleic acid sequence encoding a *Zea mays* P-Zm.CPC214tr2 promoter.

SEQ ID NO: 21 sets forth a nucleic acid sequence encoding a *Oryza sativa* P-Os.CPC214 promoter.

SEQ ID NOs: 22-23 set forth primer sequences.

DETAILED DESCRIPTION OF THE INVENTION

Figure 1:
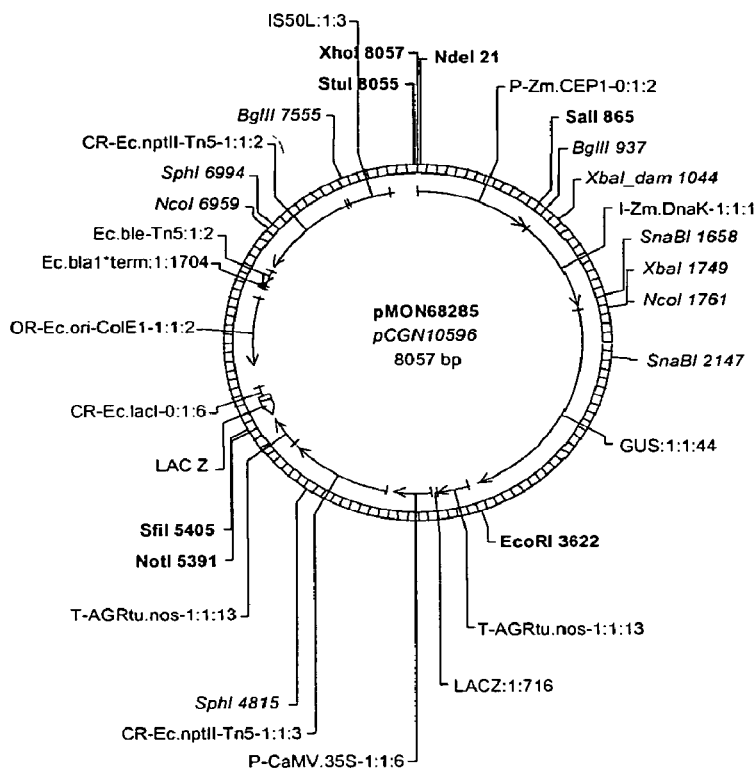
FIG. 1 depicts pMON68285.
Figure 2:
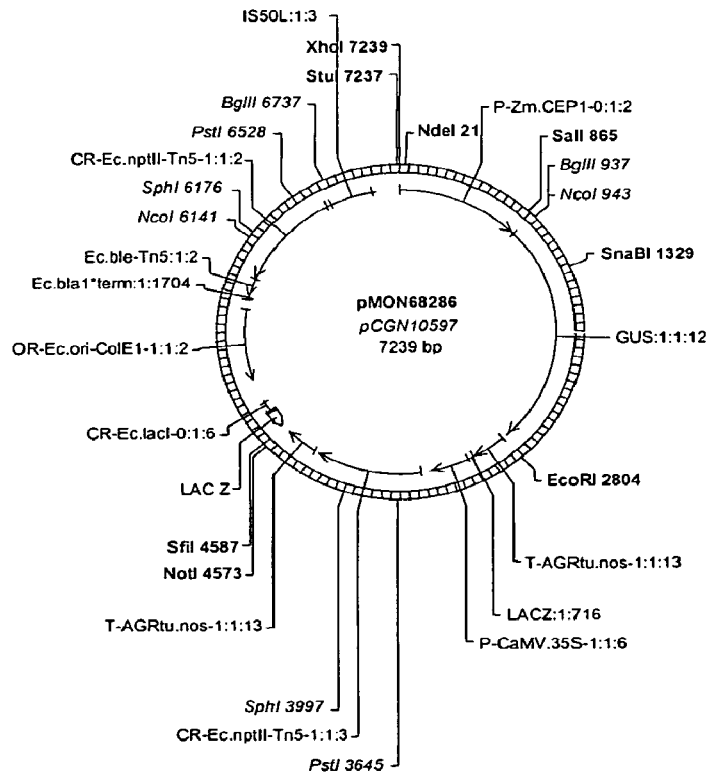
FIG. 2 depicts pMON68286.
Figure 3:
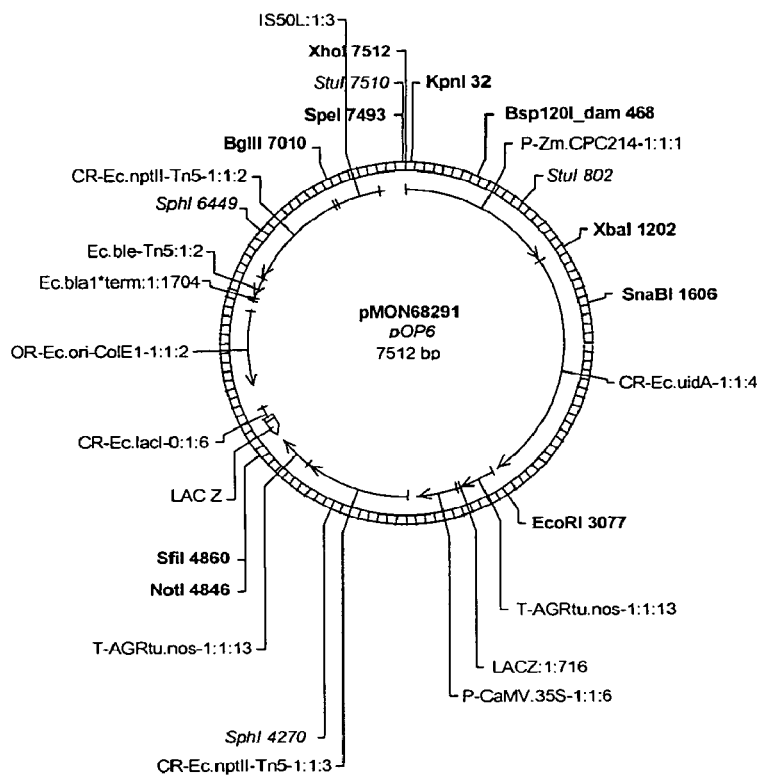
FIG. 3 depicts pMON68291.
Figure 4:
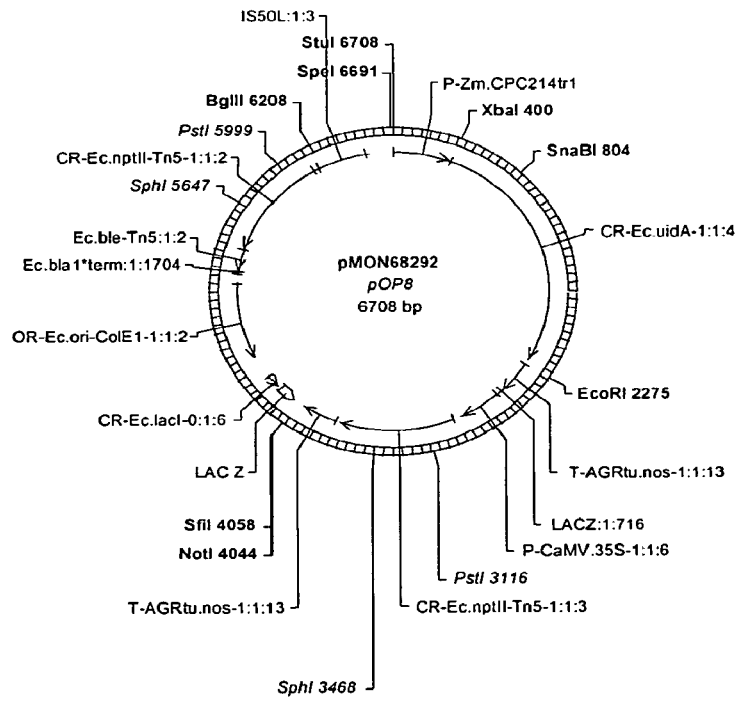
FIG. 4 depicts pMON68292.
Figure 5:
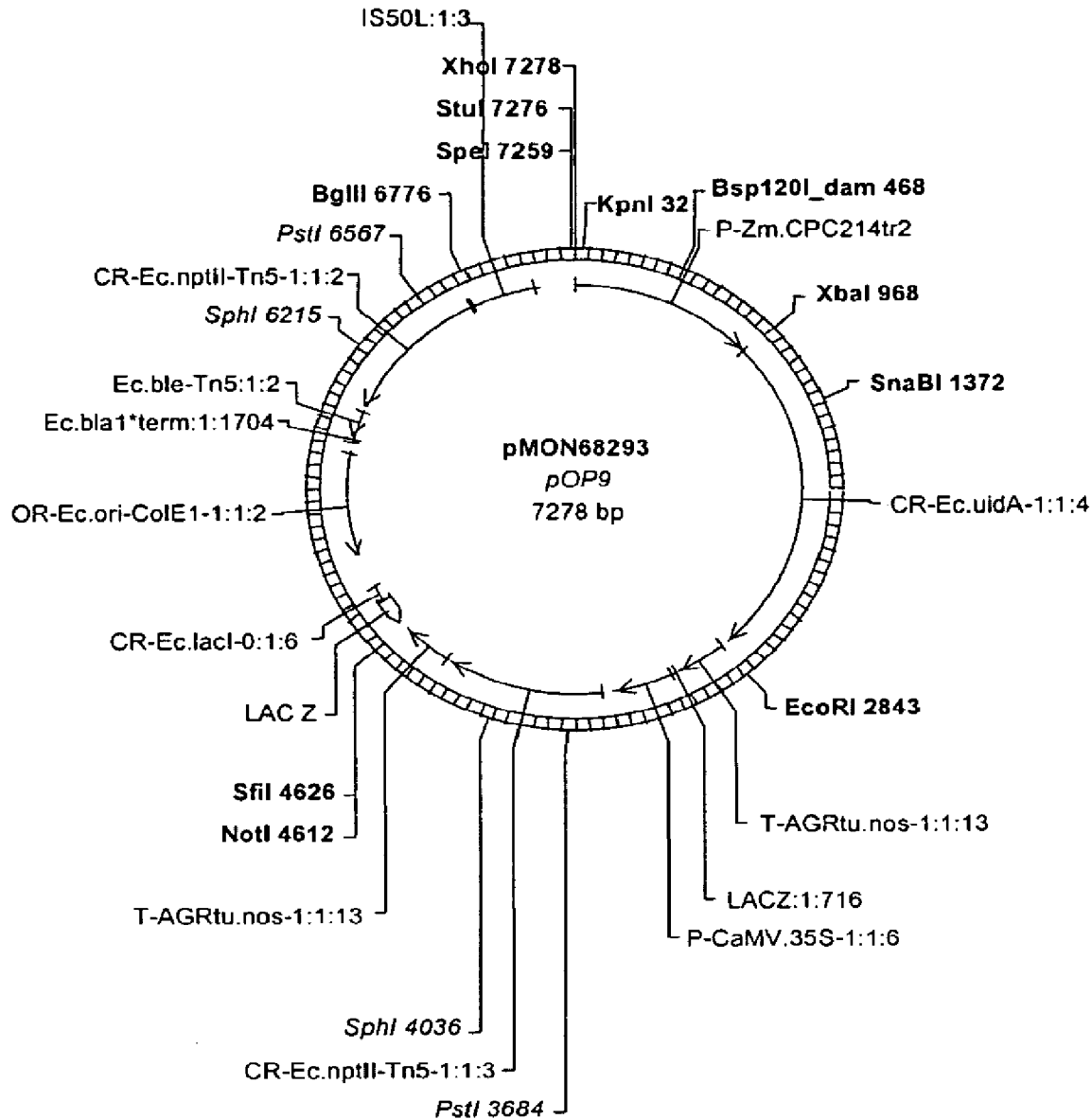
FIG. 5 depicts pMON68293.

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the term "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for DNA bases as set forth at 37 CFR § 1.822 is used.

Promoters

As used herein, the term "promoter" refers to a polynucleotide molecule that, in its native state, is located upstream or 5' to a translational start codon of an open reading frame (or protein-coding region) and that is involved in recognition and binding of RNA polymerase II and other proteins (trans-acting transcription factors) to initiate transcription. A "plant promoter" is a native or non-native promoter that is functional in plant cells. Constitutive plant promoters are functional in most or all tissues of a plant throughout plant development. Any plant promoter can be used as a 5' regulatory element for modulating expression of a particular gene or genes operably associated thereto. When operably linked to a transcribable polynucleotide molecule, a promoter typically causes the transcribable polynucleotide molecule to be transcribed in a manner that is similar to that of which the promoter is normally associated. Plant promoters can include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. Thus, the design, construction, and use of chimeric or hybrid promoters comprising at least one cis-element of SEQ ID NOs: 11, 18, 19, and 20 for modulating the expression of operably linked polynucleotide sequences is encompassed by the present invention.

As used herein, the term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

In one embodiment, the promoters of the present invention comprise multiple cis-elements each of which confers a different aspect to the overall control of gene expression. In a preferred embodiment, cis-elements from the polynucleotide molecules of SEQ ID NOs: 11, 18, 19, and 20 are identified using computer programs designed specifically to identify cis-element, domains, or motifs within sequences. Cis-elements may either positively or negatively regulate gene expression, depending on the conditions. The present invention therefore encompasses cis-elements of the disclosed promoters.

As used herein, the term "substantially homologous" refers to polynucleotide molecules that demonstrate a substantial percent sequence identity with the promoters provided herein, wherein the polynucleotide molecules function in plants to direct transcription and have at least about 70% sequence identity, at least about 80% sequence identity, at least about 90% sequence identity, or even greater sequence identity, such as 98% or 99% sequence identity with the polynucleotide sequences of the promoters described herein. Polynucleotide molecules that are capable of regulating transcription of operably linked transcribable polynucleotide molecules and are substantially homologous to the polynucleotide sequences of the promoters provided herein are encompassed within the scope of this invention.

As used herein, the term "percent sequence identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more polynucleotide sequences may be to a full-length polynucleotide sequence or a portion thereof, or to a longer polynucleotide sequence.

As used herein, the term "homology" refers to the level of similarity or percent identity between polynucleotide sequences in terms of percent nucleotide positional identity, i.e., sequence similarity or identity. As used herein, the term homology also refers to the concept of similar functional properties among different polynucleotide molecules, e.g., promoters that have similar function may have homologous cis-elements. Polynucleotide molecules are homologous when under certain conditions they specifically hybridize to form a duplex molecule. Under these conditions, referred to as stringency conditions, one polynucleotide molecule can be used as a probe or primer to identify other polynucleotide molecules that share homology.

The term "stringent conditions" is functionally defined with regard to the hybridization of a nucleic-acid probe to a target nucleic acid (i.e., to a particular nucleic-acid sequence of interest) by the specific hybridization procedure discussed in *Molecular Cloning: A Laboratory Manual*, $3^{rd}$ edition Volumes 1, 2, and 3. J. F. Sambrook, D. W. Russell, and N. Irwin, Cold Spring Harbor Laboratory Press, 2000 (referred to herein as Sambrook, et al.). Accordingly, the nucleotide sequences of the invention may be used for their ability to selectively form duplex molecules with complementary stretches of polynucleotide molecule fragments. Depending on the application envisioned one would desire to employ varying conditions of hybridization to achieve varying degrees of selectivity of probe towards target sequence.

For applications requiring high selectivity, one will typically desire to employ relatively high stringent conditions to form the hybrids, e.g., one will select relatively low salt and/or high temperature conditions, such as provided by about 0.02 M to about 0.15 M NaCl at temperatures of about 50° C. to about 70° C. A high stringent condition, for example, is to wash the hybridization filter at least twice with high-stringency wash buffer (0.2×SSC, 0.1% SDS, 65° C.). Appropriate moderate stringency conditions that promote DNA hybridization, for example, 6.0× sodium chloride/sodium citrate (SSC) at about 45° C., followed by a wash of 2.0×SSC at 50° C., are known to those skilled in the art. Additionally, the salt concentration in the wash step can be selected from a low stringency of about 2.0×SSC at 50° C. to a high stringency of about 0.2×SSC at 50° C. Additionally, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little mismatch between the probe and the template or target strand. Detection of polynucleotide molecules via hybridization is well known to those of skill in the art, and the teachings of U.S. Pat. Nos. 4,965,188 and 5,176,995 are exemplary of the methods of hybridization analyses.

Homology can also be determined by computer programs that align polynucleotide sequences and estimate the ability of polynucleotide molecules to form duplex molecules under certain stringency conditions. Polynucleotide molecules from different sources that share a high degree of homology are referred to as "homologues".

Methods well known to one skilled in the art may be used to identify promoters of interest having activity similar to the promoters described herein. For example, cDNA libraries may be constructed using cells or tissues of interest and screened to identify genes having an expression pattern similar to that of the promoters described herein. The cDNA sequence for the identified gene may then be used to isolate the gene's promoter for further characterization. See for example U.S. Pat. Nos. 6,096,950, 5,589,583; and 5,898,096, incorporated herein by reference. Alternately, transcriptional profiling or electronic northern techniques may be used to identify genes having an expression pattern similar to that of the promoters described herein. Once these genes have been identified, their promoters may be isolated for further characterization. See for example U.S. Pat. Nos. 6,506,565 and 6,448,387, incorporated herein by reference.

The electronic northern technique refers to a computer-based sequence analysis which allows sequences from multiple cDNA libraries to be compared electronically based on parameters the researcher identifies including abundance in EST populations in multiple cDNA libraries, or exclusively to EST sets from one or combinations of libraries. The transcriptional profiling technique is a high-throughput method used for the systematic monitoring of gene expression profiles for thousands of genes. This DNA chip-based technology arrays thousands of cDNA sequences on a support surface. These arrays are simultaneously hybridized to a population of labeled cDNA probes prepared from RNA samples of different cell or tissue types, allowing direct comparative analysis of expression. This approach may be used for the isolation of regulatory sequences such as promoters associated with those genes.

In another embodiment, the promoter disclosed herein can be modified. Those skilled in the art can create promoters that have variations in the polynucleotide sequence. The polynucleotide sequences of the promoters of the present invention as shown in SEQ ID NOs: 11, 18, 19, and 20 may be modified or altered to enhance their control characteristics. One preferred method of alteration of a polynucleotide sequence is to use PCR to modify selected nucleotides or regions of sequences. These methods are well known to those of skill in the art. Sequences can be modified, for example by insertion, deletion, or replacement of template sequences in a PCR-based DNA modification approach. A "variant" is a promoter containing changes in which one or more nucleotides of an original promoter is deleted, added, and/or substituted, preferably while substantially maintaining promoter function. For example, one or more base pairs may be deleted from the 5' or 3' end of a promoter to produce a "truncated" promoter. One or more base pairs can also be inserted, deleted, or substituted internally to a promoter. In the case of a promoter fragment, variant promoters can include changes affecting the transcription of a minimal promoter to which it is operably linked. A minimal or basal promoter is a polynucleotide molecule that is capable of recruiting and binding the basal transcription machinery. One example of basal transcription machinery in eukaryotic cells is the RNA polymerase II complex and its accessory proteins. Variant promoters can be produced, for example, by standard DNA mutagenesis techniques or by chemically synthesizing the variant promoter or a portion thereof.

Novel chimeric promoters can be designed or engineered by a number of methods. Many promoters contain cis-elements that activate, enhance or define the strength and/or specificity of the promoter. For example promoters may contain "TATA" boxes defining the site of transcription initiation and other cis-elements located upstream of the transcription initiation site that modulate transcription levels. For example, a chimeric promoter may be produced by fusing a first promoter fragment containing the activator cis-element from one promoter to a second promoter fragment containing the activator cis-element from another promoter; the resultant chimeric promoter may cause an increase in expression of an operably linked transcribable polynucleotide molecule. Promoters can be constructed such that promoter fragments or elements are operably linked, for example, by placing such a fragment upstream of a minimal promoter. The cis-elements and fragments of the present invention can be used for the construction of such chimeric promoters. Methods for construction of chimeric and variant promoters of the present invention include, but are not limited to, combining control elements of different promoters or duplicating portions or regions of a promoter (see for example, U.S. Pat. Nos. 4,990,607; 5,110,732; and 5,097,025, all of which are herein incorporated by reference). Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

In another embodiment, a promoter comprising the polynucleotide sequence shown in SEQ ID NOs: 11, 18, 19, and 20 includes any length of said polynucleotide sequence that has promoter activity, e.g., is capable of regulating transcription of an operably linked transcribable polynucleotide molecule. For example, the promoters as disclosed in SEQ ID NOs: 11, 18, 19, and 20 may be truncated or portions deleted and still be capable of regulating transcription of an operably linked polynucleotide molecule. In particular embodiments, promoter fragments may be provided comprising at least about 30, 50, 70, 90, 110, 125, 150 or about 200 or longer nucleotides. In specific embodiments, these fragments may comprise contiguous portions of the sequences disclosed in SEQ ID NOs: 11, 18, 19, and 20.

In a related embodiment, a cis-element of the disclosed promoters may confer a particular specificity such as conferring enhanced expression of operably linked polynucleotide molecules in certain tissues and therefore is also capable of regulating transcription of operably linked polynucleotide molecules. Consequently, any fragments, portions, or regions of the promoters comprising the polynucleotide sequence shown in SEQ ID NOs: 11, 18, 19, and 20 can be used as regulatory polynucleotide molecules, including but not limited to cis-elements or motifs of the disclosed polynucleotide molecules. Substitutions, deletions, insertions or any combination thereof can be combined to produce a final construct. Fragments in particular may be generated in large numbers and screened for promoter activity in transient or whole-plant assays using routine procedures well known to those of skill in the are. For example, fragments may be generated using partial or complete restriction digests with various endonucleases as well as with manual shearing or other techniques as desired. The fragments may be cloned into an expression vector and operably linked to a selectable or screenable marker gene to assay for promoter activity. In this manner, multiple fragments of a starting full length promoter sequence may be readily identified that have a desired promoter activity. Examples of such methodology may be found in U.S. Pat. No. 6,747,189, the entire disclosure of which is specifically incorporated herein by reference.

Polynucleotide Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. Preferably, the two polynucleotide molecules are part of a single contiguous polynucleotide molecule and more preferably are adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, Sambrook, et al.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see for example, U.S. Pat. Nos. 5,659,122 and 5,362,865; and U.S. Patent Publication No. 2002/0192812, herein incorporated by reference). These additional upstream and downstream regulatory polynucleotide molecules may be derived from a source that is native or heterologous with respect to the other elements present on the promoter construct.

Thus, constructs of the present invention comprise promoters such as those provided in SEQ ID NOs: 11, 18, 19, and 20 or modified as described above, operatively linked to a transcribable polynucleotide molecule so as to direct transcription of said transcribable polynucleotide molecule at a desired level or in a desired tissue or developmental pattern upon introduction of said construct into a plant cell. In some cases, the transcribable polynucleotide molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into constructs of the present invention include, for example, DNA molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or DNA molecule that is introduced into a recipient cell. The type of DNA included in the exogenous DNA can include DNA that is already present in the plant cell, DNA from another plant, DNA from a different organism, or a DNA generated externally, such as a DNA molecule containing an antisense message of a gene, or a DNA molecule encoding an artificial or modified version of a gene.

The promoters of the present invention can be incorporated into a construct using marker genes as described and tested in transient analyses that provide an indication of gene expression in stable plant systems. As used herein the term "marker gene" refers to any transcribable polynucleotide molecule whose expression can be screened for or scored in some way. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable polynucleotide molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Preferred marker genes for transient analyses of the promoters or promoter fragments of the present invention include a GUS gene (U.S. Pat. No. 5,599,670, herein incorporated by reference) or a GFP gene (U.S. Pat. No. 5,491,084, herein incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a polynucleotide molecule of the present invention as shown in SEQ ID NOs: 11, 18, 19, and 20 or fragments, variants, or derivatives thereof is incorporated into a construct such that a promoter of the present invention is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061; 5,633,435; and 6,040,497; and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., *Plant J.*, 4:833-840 (1993) and Misawa et al., *Plant J.*, 6:481-489 (1994) for norflurazon tolerance; a polynucleotide molecule encoding acetohydroxyacid synthase (AHAS, aka ALS) described in Sathasiivan et al. *Nucl. Acids Res.*, 18:2188-2193 (1990) for tolerance to sulfonylurea herbicides; and the bar gene described in DeBlock, et al. *EMBO J.*, 6:2513-2519 (1987) for glufosinate and bialaphos tolerance.

In one preferred embodiment, a polynucleotide molecule of the present invention as shown in SEQ ID NOs: 11, 18, 19, and 20 or fragments, variants, or derivatives thereof is incorporated into a construct such that a promoter of the present invention is operably linked to a transcribable polynucleotide molecule that is a gene of agronomic interest. As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait.

A gene of agronomic interest that provides a beneficial agronomic trait to crop plants may be, for example, including, but not limited to genetic elements comprising herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407; and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Patent Publication No. 2003/0028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference.

Alternatively, a transcribable polynucleotide molecule can effect the above mentioned phenotypes by encoding a non-translatable RNA molecule that causes the targeted inhibition of expression of an endogenous gene, for example via antisense, RNAi, or cosuppression-mediated mechanisms. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest is useful for the practice of the present invention.

The constructs of the present invention, in one embodiment, are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also may contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants and Plant Cells

As used herein, the term "transformed" refers to a cell, tissue, organ, or organism into which has been introduced a foreign polynucleotide molecule, such as a construct. Preferably, the introduced polynucleotide molecule is integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,635,055; 5,824,877; 5,591,616; 5,981,840; and 6,384,301; and protoplast transformation as illustrated in U.S. Pat. No. 5,508,184, all of which are incorporated herein by reference.

Methods for specifically transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including *indica* and *japonica* varieties); sorghum (*Sorghum bicolor*); sugar cane (*Saccharum* sp); tall fescue (*Festuca arundinacea*); turfgrass (*Agrostis*); wheat (*Triticum aestivum*), and alfalfa (*Medicago sativa*). It is apparent to those of skill in the art that a number of transformation methodologies can be used and modified for production of stable transgenic plants from any number of target crops of interest.

In certain embodiments, the invention provides a method of making a vegetable oil, comprising the steps of incorporating into the genome of an oilseed plant a promoter of the present invention operably linked to a transcribable polynucleotide molecule conferring altered oil and/or protein content, growing the oilseed plant to produce oilseeds, and extracting the oil and/or protein from the oilseed.

The transformed plants are generally analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest. The terms "seeds" and "kernels" are understood to be equivalent in meaning. The term kernel is frequently used in describing the seed of a corn or rice plant. In all plants the seed is the mature ovule consisting of a seed coat, embryo, aleurone, and an endosperm.

The phrase "cell proliferation" refers to cells undergoing mitotic cell divisions, such as in rapidly growing tissues.

The term "micronutrient content" means the amount of micronutrients, i.e., vitamins A, E, K, tocopherols, tocotrienols, or carotenoids, within a seed expressed on a per weight basis.

The phrase "oil content" means oil level, which may be determined, for example, by low-resolution $^1$H nuclear magnetic resonance (NMR) (Tiwari et al., *JAOCS*, 51:104-109 (1974) or Rubel, *JAOCS*, 71:1057-1062 (1994)) or near infrared transmittance (NIT) spectroscopy (Orman, et al. *JAOCS*, 69(10):1036-1038 (1992); Patrick, et al., *JAOCS*, 74(3):273-276 (1997)).

The term "protein quality" means the level of one or more essential amino acids, whether free or incorporated in protein, namely histidine, isoleucine, leucine, lysine, methionine, cysteine, phenylalanine, tyrosine, threonine, tryptophan, and valine.

EXAMPLES

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

Example 1

Isolation of the Promoter P-ZmCEP1

As a first step in the isolation of a proliferation phase embryo promoter from *Zea mays*, candidate Expressed Sequence Tags (ESTs) were identified by electronic library subtraction using proprietary Monsanto embryo EST libraries as the target tissue and non-kernel libraries as the background tissue. Background libraries included root, shoot, stem, seedling, tassel silk, pollen and flower EST libraries. ESTs identified electronically as potentially expressed only in early embryos were further characterized by hybridization.

Clones containing the ESTs of interest were used as a template for PCR. Southern blots of the PCR products were prepared. Blots were hybridized to radiolabelled cDNA derived from leaf, root, tassel, 5 dap (days after pollination) whole kernels and 10 dap germ tissue. Clones that were not eliminated by hybridization to non-kernel-derived cDNA's were used as probes against SMART™ cDNAs (Clontech, Palo Alto, Calif.) derived from a panel of kernel and non kernel tissues: 3 dap whole kernel, 5 dap whole kernel, 7 dap whole kernel, 10 dap germ, 14 dap germ, 19 dap germ, 10 dap endosperm, 14 dap endosperm, 19 dap endosperm, leaf, primary root, secondary root, silk, stem and tassel. An EST clone, designated CEP1, hybridized strongly to 10 and 14 dap embryo-derived cDNA and weakly to 7 dap whole kernel- and 10 dap endosperm-derived cDNA. The sequence for this EST is SEQ ID NO: 1.

Total RNA from 10 DAP whole kernels from cultivar LH59 was used as a template for 5' RACE reactions (SMART RACE cDNA Amplification Kit, Clontech). RNA was extracted using the protocol of Opsahl-Ferstad et al., *Plant Journal*, 12:235-246 (1997) with the following modifications: 50 mM βME was added to the extraction buffer and a TRIZOL LS (Invitrogen, Carlsbad, CA) wash step was added as a final clean-up. A gene-specific primer (SEQ ID NO: 2) for the 5' RACE reaction was designed based on the CEP1 EST sequence (SEQ ID NO: 1). Products from the RACE reaction were cloned into the TOPO TA cloning vector (Invitrogen) and sequenced to yield a consensus sequence (SEQ ID NO: 7). Based on this consensus sequence, two different sets of primer pairs, SEQ ID NOs: 3 and 4 and SEQ ID NOs: 5 and 6, were designed for use with the Universal GenomeWalker Kit (Clontech). Fragments generated from genome walking were cloned into the TOPO TA cloning vector. The 1264 base pair CEP1 upstream genomic sequence (SEQ ID NO: 8) was based on consensus sequence of three clones each from four different GenomeWalker reactions. Primers (SEQ ID NOs: 9 and 10) were designed based on the genomic sequence to amplify the 930 base pair promoter region P-Zm.CEP1 (SEQ ID NO: 11). The 5' primer (SEQ ID NO: 9) contained an XhoI site and the 3' primer (SEQ ID NO: 10) contained BglII and NcoI sites to facilitate cloning into expression cassettes.

Example 2

Isolation of the Promoter P-Zm.CPC214

As a first step in the isolation of a proliferation phase embryo promoter from *Zea mays* using cDNA-AFLPs (amplified fragment length polymorphism, Vos, P., et al., *Nucleic Acids Research*, 23:4407-4414 (1995)), cDNAs expressed early in kernel development were identified by performing AFLP analysis on cDNAs derived from a variety of kernel and non-kernel tissues. Briefly, SMART cDNA libraries were prepared from mRNA isolated from *Z. mays* variety LH59 according to the manufacturer's instructions (Clontech). The mRNA was isolated from whole kernel at 3, 5, and 7 dap; germ at 10, 14, and 19 dap; endosperm at 10, 14, and 19 dap; leaf, silk, stem, tassel, 1° root and 2° root. Five hundred micrograms of amplified SMART cDNA was used for AFLP analysis using the Gibco-BRL small genome AFLP II Kit (Invitrogen, Carlsbad, Calif.) according to manufacturer's instructions. The resulting bands were visualized after electrophoresis through 6% acrylamide/8M Urea sequencing gels. Bands observed only in whole kernel-, germ-, or embryo-derived cDNAs were excised from the gel.

The DNA was eluted by placing the acrylamide band in 50 μl of TE (10 mM Tris-HCl (pH 8.0); 1 mM EDTA) and allowing the band to elute at ambient temperature overnight. After a brief centrifugation, 0.75 ul of supernatant was used as template for PCR amplification. Twenty ul of Preamp primer mix 2 (Gibco-BRL small genome AFLP II Kit, Invitrogen), 2.5 ul 10× PCR buffer with 15 mM MgCl (PE Applied Biosystems, Foster City, CA), 2.5 units AMPLITAQ DNA Polymerase (PE Applied Biosystems) and 2 ul water were added to the DNA template. Amplification conditions were as follows: 25 cycles of 94° C. for 30 seconds, 56° C. for 60 seconds, and 72° C. for 2 minutes followed by 1 cycle of 72° C. for 2 minutes. The resulting PCR products were purified using the QIAQUICK PCR Purification Kit (Qiagen, Valencia CA) according to manufacturer's instructions and then were separated on agarose gel. Gels were exposed to short wave UV light for 2-3 minutes. The DNA was denatured in 0.5N NaOH; 1.5 M NaCl and transfeffed to NYTRAN Plus (Schleicher & Schuell, Keene, NH) using the TurboBlotter system (Schleicher & Schuell). Blots were hybridized to radiolabelled cDNA derived from maize whole kernel at 3, 5, or 7 days after pollination (dap); germ at 10 dap; leaf, root and tassel. Additionally some blots were hybridized to cDNA derived from maize silk, stem and/or endosperm at 14 dap. Candidates not eliminated by cDNA hybridization were used as probes against SMART™cDNAs (Clontech) derived from a panel of maize kernel and non kernel tissues: 3 dap whole kernel, 5 dap whole kernel, 7 dap whole kernel, 10 dap germ, 14 dap germ, 19 dap germ, 10 dap endosperm, 14 dap endosperm, 19 dap endosperm, leaf, primary root, secondary root, silk, stem and tassel. The DNA fragment CPC214 hybridized to 10 dap germ-derived eDNA and 10 dap endosperm-derived cDNA and was subcloned in pCR2.1 TOPO (Invitrogen). The sequence of CPC214 was determined (SEQ ID NO: 12).

Total RNA from 10 DAP whole kernels from cultivar LH59 was used as a template for 5' RACE reactions (SMART RACE cDNA Amplification Kit, Clontech). RNA was extracted using the protocol of Opsahl-Ferstad et al., Plant Journal, 12:235-246 (1997) with the following modifications: 50 mM βME was added to the extraction buffer and a TRIZOL LS (Invitrogen) wash step was added as a final clean-up. A gene-specific primer (SEQ ID NO: 13) for the 5' RACE reaction was designed based on the CPC214 EST sequence (SEQ ID NO: 12). Products from the RACE reaction were cloned into the TOPO TA cloning vector (Invitrogen) and sequenced to yield a consensus sequence (SEQ ID NO: 14). Based on this consensus sequence, a primer pair, SEQ TD NOs: 15 and 16, were designed for use with the Universal GenomeWalker Kit (Clontech). Fragments generated from genome walking were cloned into the TOPO TA cloning vector. The CPC214 genomic sequence (SEQ ID NO: 17) was based on consensus sequence of at least four clones each from three different GenomeWalker reactions. One of the clones matched the consensus sequence exactly.

The CPC214 genomic sequence (SEQ ID NO: 17) was used as the substrate for amplifying a promoter sequence, P-Zm.CPC214 (SEQ ID NO: 18), with two primers (SEQ ID NOs: 22 and 23). This fragment was cloned into pMON77954 yielding pMON68291. A truncated version of this element, P-Zm.CPC214tr1, was made by digesting the plasmid pMON68291 with StuI and ligating the plasmid together thus creating a version (SEQ ID NO: 19) lacking 797 bases of 5' sequence (pMON68292). A third version was constructed by digesting the promoter (SEQ ID NO: 18) with PstI and NcoI and filling in the 5' overhangs with Klenow enzyme. This truncated version, P-Zm.CPC214tr2 (SEQ ID NO: 20), was digested with XhoI and XbaI and cloned into XhoI/XbaI digested pMON77954 yielding pMON68293.

Example 3

Isolation of the Promoter P-Os.CPC214

The Zm.CPC214 RACE consensus sequence (SEQ ID NO: 14) was used to screen the Monsanto Maize Unigene Database. A matching maize Unigene sequence was identified and used to Blast a rice genomic sequence library. A homologous rice sequence was identified. Through the analysis of the genome annotation features around the locus of the gene, the optimal promoter sequence was determined to be from 801 bp upstream of the translation start site to the translation start site, not including the translation start site. The promoter was designated P-Os.CPC214 (SEQ ID NO: 21).

Example 4

Constructs for Corn Transformation

The promoters described above were operably linked to the marker gene, *Escherichia coli* uidA, in a construct to demonstrate expression in corn. Some constructs contained the 5' UTR from the corn heat shock protein, HSP70 (Zm.DnaK) (U.S. Pat. No. 5,424,412, Brown, et al.). All constructs contained the 3' UTR from the nopaline synthase 3' termination regions (nos) (Bevan et al., *Nucl. Acid Res.*, 11:369 (1983)). Table 1 lists the promoter construct specifics.

TABLE 1

Corn Transformation Constructs

| Construct | Promoter | SEQ ID | 5' UTR | Marker gene | 3' UTR | Fig. |
|---|---|---|---|---|---|---|
| pMON68285 | P-Zm.CEP1 | 11 | Zm.DnaK | uidA | nos | 1 |
| pMON68286 | P-Zm.CEP1 | 11 | None | uidA | nos | 2 |
| pMON68291 | P-Zm.CPC214 | 18 | None | uidA | nos | 3 |
| pMON68292 | P-Zm.CPC214tr1 | 19 | None | uidA | nos | 4 |
| pMON68293 | P-Zm.CPC214tr2 | 20 | None | uidA | nos | 5 |

The constructs described in Table 1 were transformed into corn line H99 by standard bombardment methods known to those skilled in the art (see for example Songstad, D. D., et al. 1996. Production of transgenic maize plants and progeny was carried out by bombardment of Hi II immature embryos. *In Vitro Cell. Dev. Biol.—Plant.* 32:179-183). Ears of maize H99 plants were collected 10-13 days after pollination from greenhouse grown plants and sterilized. Immature zygotic embryos of 1.2-1.5 mm were excised from the ear and incubated at 28° C. in the dark for 3-5 days before use as target tissue for bombardment. DNA comprising an isolated expression cassette containing the selectable marker for kanamycin resistance (NPTII gene) and the screenable marker for β-D-Glucuronidase (GUS gene) was gel purified and used to coat 0.6 micron gold particles (Bio-Rad, Hercules, Calif.) for bombardment. Macro-carriers were loaded with the DNA-coated gold particles (Bio-Rad). The embryos were transferred onto osmotic medium scutellum side up. A PDS 1000/He biolistic gun is used for transformation (Bio-Rad). Bombarded embryos were cultured, transgenic events were selected with kanamycin, and transgenic plants regenerated.

Example 5

Promoter Characterization in Transgenic Plants

Plants (R0) transformed with the constructs described above were crossed with non-transgenic H99 plants. The F1 plants and the resulting F2 seed were used for characterization. The details of developmental stages, tissue type and replications used for GUS (β-D-glucuronidase, the product of the *E. coli* uidA gene) reporter gene analysis are given in Table 2.

TABLE 2

Tissue Sectioning for Histochemical GUS Staining

| Developmental Stage | Replications | Organ/Tissue |
|---|---|---|
| Imbibed seed | 6 seeds | Seed. |
| 3 days after germination | 6 seedlings | Root and shoot apex |
| V3 stage | 2 plants | Root, $2^{nd}$ leaf from top |
| V7 stage | 2 plants | Root, source leaf ($2^{nd}$ leaf from top), sink leaf (emerging leaf), node &inter-node, cob &tassel primordia |
| VT stage | 2 plants | Root, source leaf ($3^{rd}$ leaf from top), senescing leaf ($10^{th}$ leaf from top), node & inter-node, cob, spikelet, pollen |
| 7 DAP | 6 seeds/cob -2 plants | Kernel |
| 14 DAP | 6 seeds/cob -2 plants | Kernel |
| 21 DAP | 6 seeds/cob -2 plants | Kernel |
| 35 DAP | 6 seeds/cob -2 plants | Kernel |

GUS activity was qualitatively measured using methods known to those skilled in the art (see for example Jefferson, R. A., Kavanagh, T. A. and Bevan, M. W. 1987 GUS fusions: β-Glucuronidase as a Sensitive and Versatile Gene Fusion Marker in Higher Plants. *EMBO Journal* 6: 3901-3907). For qualitative analysis, whole tissue sections are incubated with the GUS staining solution X-Gluc (5-bromo-4-chloro-3-indolyl-β-glucuronide) (1 mg/ml) for an appropriate length of time, rinsed, and visually inspected for blue coloration.

Corn plants representing 6 F1 events transformed with the pMON68285 vector containing the P-Zm.CEP1 promoter (SEQ ID NO: 11) operably linked to the Zm.DnaK intron and the GUS transgene were analyzed for GUS activity as described above. Qualitative GUS analysis revealed that the expression was seen mostly in the embryo, particularly in the coleoptiles and coleorhizal region of the embryo. The expression in the embryos could be observed as early as 7 days after pollination (DAP) and continued until 35 DAP. Imbibed seed embryos did not reveal any blue color. The cob primordia at VT stage also showed expression.

Corn plants representing 6 F1 events transformed with the pMON68286 vector containing the P-Zm.CEP1 promoter (SEQ ID NO: 11) operably linked to the GUS transgene were analyzed for GUS activity as described above. Qualitative GUS analysis revealed that the expression was seen in the embryo at 21 and 35 DAP. Imbibed seed embryos did not reveal any blue color. The cob primordia at VT stage also showed expression. Similar results are observed for SEQ ID NOs: 18, 19 and 20.

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

What is claimed is:

1. A polynucleotide molecule comprising a sequence selected from the group consisting of SEQ ID NOs: 18, 19, 20, or a fragment of at least 50 contiguous nucleotides thereof having promoter activity, wherein said polynucleotide molecule is operably linked to a heterologous transcribable nucleic acid.

2. The polynucleotide molecule of claim 1, wherein said polynucleotide molecule comprises the polynucleotide sequence of SEQ ID NO: 18.

3. The polynucleotide molecule of claim 1, wherein said polynucleotide molecule comprises the polynucleotide sequence of SEQ ID NO: 19.

4. The polynucleotide molecule of claim 1, wherein said polynucleotide molecule comprises the polynucleotide sequence of SEQ ID NO: 20.

5. An expression vector comprising the polynucleotide molecule of claim 1.

6. The polynucleotide molecule of claim 1, wherein said heterologous transcribable nucleic acid is a nucleic acid of agronomic interest.

7. The polynucleotide molecule of claim 1, wherein said heterologous transcribable nucleic acid is a marker gene.

8. A transgenic plant stably transformed with the polynucleotide molecule of claim 1.

9. The transgenic plant of claim 8, wherein said plant is a monocotyledon selected from the group consisting of wheat, maize, rye, rice, oat, barley, turfgrass, sorghum, millet and sugarcane.

10. The transgenic plant of claim 8, wherein said transcribable nucleic acid confers altered cell proliferation in the embryo, aleurone, or both to said transgenic plant.

11. The transgenic plant of claim 8, wherein said transcribable nucleic acid confers altered oil content in the embryo, aleurone, or both to said transgenic plant.

12. The transgenic plant of claim 8, wherein said transcribable nucleic acid confers altered protein quality in the embryo, aleurone, or both to said transgenic plant.

13. The transgenic plant of claim 8, wherein said transcribable nucleic acid confers altered micronutrient content to said transgenic plant.

14. A seed of the transgenic plant of claim 8, wherein said seed comprises said polynucleotide molecule.

15. A part of the transgenic plant of claim 8, wherein said part comprises said polynucleotide molecule.

16. The part of claim 15, further defined as a cell of the transgenic plant of claim 8, wherein said cell comprises said polynucleotide molecule.

17. A method of producing a vegetable oil, comprising the steps of:
  a) incorporating in the genome of an oilseed producing plant the polynucleotide molecule of claim 1; wherein said transcribable nucleic acid confers altered oil content to said oilseed;
  b) growing the plant to produce oil; and
  c) extracting the oil from seeds of the plant.

18. A method of making protein, comprising the steps of:
  a) obtaining the transgenic plant of claim 8;
  b) growing the plant to produce protein; and
  c) extracting protein from the plant.

19. The polynucleotide molecule of claim 1, wherein said polynucleotide molecule comprises a fragment of at least 90 contiguous nucleotides of SEQ ID NO:18 having promoter activity.

20. The polynucleotide molecule of claim 1, wherein said polynucleotide molecule comprises a fragment of at least 200 contiguous nucleotides of SEQ ID NO:18 having promoter activity.

21. The transgenic plant of claim 8, wherein said polynucleotide molecule comprises SEQ ID NO:18.

22. The transgenic plant of claim 8, wherein said polynucleotide molecule comprises SEQ ID NO:19.

23. The transgenic plant of claim 8, wherein said polynucleotide molecule comprises SEQ ID NO:20.

24. The transgenic plant of claim 8, wherein said polynucleotide molecule comprises a fragment of at least 90 contiguous nucleotides of SEQ ID NO:18 having promoter activity.

25. The transgenic plant of claim 8, wherein said polynucleotide molecule comprises a fragment of at least 200 contiguous nucleotides of SEQ ID NO:18 having promoter activity.

26. The seed of claim 14, wherein said polynucleotide molecule comprises SEQ ID NO:18.

27. The seed of claim 14, wherein said polynucleotide molecule comprises SEQ ID NO:19.

28. The seed of claim 14, wherein said polynucleotide molecule comprises SEQ ID NO:20.

29. The seed of claim 14, wherein said polynucleotide molecule comprises a fragment of at least 90 contiguous nucleotides of SEQ ID NO:18 having promoter activity.

30. The seed of claim 14, wherein said polynucleotide molecule comprises a fragment of at least 200 contiguous nucleotides of SEQ ID NO:18 having promoter activity.

31. The part of claim 15, wherein said polynucleotide molecule comprises SEQ ID NO:18.

32. The part of claim 15, wherein said polynucleotide molecule comprises SEQ ID NO:19.

33. The part of claim 15, wherein said polynucleotide molecule comprises SEQ ID NO:20.

34. The part of claim 15, wherein said polynucleotide molecule comprises a fragment of at least 90 contiguous nucleotides of SEQ ID NO:18 having promoter activity.

35. The part of claim 15, wherein said polynucleotide molecule comprises a fragment of at least 200 contiguous nucleotides of SEQ ID NO:18 having promoter activity.

* * * * *